United States Patent [19]
Cavalieri et al.

[11] Patent Number: 5,407,454
[45] Date of Patent: Apr. 18, 1995

[54] LARVICIDAL LECTINS AND PLANT INSECT RESISTANCE BASED THEREON

[75] Inventors: Anthony Cavalieri, Johnson; Thomas Czapla, Urbandale; John Howard, West Des Moines; Gururaj Rao, Urbandale, all of Iowa

[73] Assignee: Pioneer Hi-Bred International, Inc., Des Moines, Iowa

[21] Appl. No.: 763,100

[22] Filed: Sep. 20, 1991

Related U.S. Application Data

[63] Continuation-in-part of Ser. No. 665,919, Mar. 4, 1991, abandoned, which is a continuation of Ser. No. 433,625, Nov. 7, 1989, abandoned.

[51] Int. Cl.$^6$ .......................... A01H 1/00; C07K 3/00; A61K 37/10; A61K 35/78
[52] U.S. Cl. ........................................ 47/58; 530/396; 530/370; 530/371; 530/372; 530/375; 530/376; 530/379; 514/8
[58] Field of Search ..................... 435/172.3; 514/8; 47/58; 424/405, 418, DIG. 8, DIG. 10; 800/205; 530/396, 370, 371, 372, 375, 376, 379

[56] References Cited

U.S. PATENT DOCUMENTS 4,870,015 9/1989 Hoffman ........................ 435/172.3
5,192,541 3/1993 Savage et al. .

FOREIGN PATENT DOCUMENTS 0186425 2/1986 European Pat. Off. ...... C12N 15/00

OTHER PUBLICATIONS

A. M. Gatehouse et al. J. Sci. Food Agne., vol. 35 (1984) pp. 373–380.
T. C. Osborn et al. Science, vol. 240 1988) pp. 207–210.
Muthukumar et al. Appl. Environ. Microbiol, vol. 53 (1987) pp. 2650–2655.
R. Shukle et al. Environment Entomology, vol. 12 (1989) pp. 787–791.
Shields, R. Nature, vol. 328 (1987) pp. 12–13.
H. D. Burger et al., British Crop Prot. Council, 1979 Proceedings, Pesis & Disease Conference, vol. s1-3 (1980) pp. 433–439.
Lance, D. R. J. Economic Entomology (1988) vol. 81 (#5) pp. 1359–1362.
Raikhel, Natasha V., et al. Proc. Natl. Acad. Sci. USA, vol. 84, pp. 6745–6749, Oct. 1987 Isolation and Characterization of a cDNA clone encoding wheat germ agglutinin.
Huesing, Joseph E., et al., Phytochemistry, vol. 30, No. 11 (1991), "Rice and Stinging Nettle Lectins: Insecticidal Activity Similar to Wheat Germ Agglutinin" (Abstract).
Balasubramaniam, Nandha Kumar, et al., Arch. Biochem. Biophys., vol. 288, No. 2 (1991) "Structural and Functional Changes Associated with Cyanogen Bromide Treatment of Wheat Germ Agglutinin" (Abstract).
Gatehouse, Angharad M. R., et al., Dep. Biol. Sci., vol. 55, No. 1 (1991) "Biochemical basis of Insect Resistance in Winged Bean (Psophocarpus tetragonolobus) Seeds" (Abstract).
Richards, Elaine H., et al., Sch. Biol. Sci., vol. 14, No. 3 (1990) "Direct Binding and Lectin–Mediated Binding of Erythrocytes to Hemocytes . . . " (Abstract).
Cohen, Ephraim, et al., Pestic. Biochem. Physiol. vol 37, No. 3 (1990) "Insect and Fungal Chitin Synthetase Activity: Specificity of Lectins as Enhancers and Nucleoside Peptides as Inhibitors" (Abstract).

(List continued on next page.)

*Primary Examiner*—David T. Fox
*Assistant Examiner*—Charles Rories
*Attorney, Agent, or Firm*—Pioneer Hi-Bred International, Inc.

[57] ABSTRACT

Selected plant lectins have been found to be larvicidal against a number of common insect pests of agricultural crops. In a preferred embodiment, plant resistance to these insects is produced by inserting into the cells of a plant a gene whose expression causes production of one or more of these lectins in larvicidal amounts.

5 Claims, 3 Drawing Sheets

OTHER PUBLICATIONS

Altabella, Teresa et al., Cent. Mol. Genet., vol. 93, No. 2 (1990) "Tobacco Plants Transformed with the Bean .Alpha.ai Gene Express an Inhibitor of Insect .alpha.-amylase in their Seeds" (Abstract).

Uhlenbruck, G., et al., Naturwissenschaften, vol. 67, No. 3 (1980) "Occurrence of the Peanut Lectin Receptor in Sericin of the Silkworm, Bombyx Mori, . . . " (Abstract).

Janzen, Daniel, et al., Phytochemistry, vol. 16, No. 2 (1977) "Toxicity of Secondary Compounds to the Seed-Eating Larvae of the Bruchid Beetle Callosobruchus Maculatus" (Abstract).

Janzen, Daniel, et al., Science, vol. 192, No. 4241 (1976) "Insecticidal Action of the Phytohemagglutinin in Black Bean on a Bruchid Beetle" (Abstract).

Huesing, Joseph E. et al.(1991) α-Amylase Inhibitor, Not Phytohemagglutinin, Explains Resistance of Common Bean seeds to Cowpea Weevil, Plant Physiol. vol. 96, pp. 993–996.

LARVICIDAL LECTINS AND PLANT INSECT RESISTANCE BASED THEREON

REFERENCE TO PRIOR COPENDING APPLICATION

This is a continuation-in-part of prior application Ser. No. 07/665,919, filed Mar. 4, 1991, now abandoned, which was a continuation of application Ser. No. 07/433,625, filed Nov. 7, 1989, now abandoned.

TECHNICAL FIELD

This invention relates to materials and methods for killing insect larvae which are harmful to plants, and materials and methods for imparting insect resistance to plants.

BACKGROUND OF THE INVENTION

Numerous insects are serious pests of common agricultural crops. One method of controlling insects has been to apply insecticidal organic or semiorganic chemicals to crops. This method has numerous, art-recognized problems. A more recent method of control of insect pests has been the use of biological control organisms which are typically natural predators of the troublesome insects. These include other insects, fungi (milky-spore) and bacteria (*Bacillus thuringiensis* cv., commonly referred to as "Bt"). However, it is difficult to apply biological control organisms to large areas, and even more difficult to cause those living organisms to remain in the treated area for an extended period. Still more recently, techniques in recombinant DNA have provided the opportunity to insert into plant cells cloned genes which express insecticidal toxins derived from biological control organisms such as Bt. This technology has given rise to additional concerns about eventual insect resistance to well-known, naturally occurring insect toxins, particularly in the face of heavy selection pressure, which may occur in some areas. Thus, a continuing need exists to identify naturally occurring insecticidal toxins which can be formed by plant cells directly by translation of a single structural gene.

European Patent Application 204,590, based upon U.S. patent application Ser. No. 725,368, describes a method of genetically modifying a plant cell to control expression of heterologous foreign structure genes, including a lectin from *Phaseolus vulgaris*. In the method, the plant cell is transformed to contain a pRi T-DNA promoter and a heterologous foreign structural gene, the promoter and the structural gene being in such position and orientation with respect to one another that the structural gene is expressible in a plant cell under control of the promoter.

Likewise, European Patent Application 186,425, based upon U.S. patent application Ser. No. 685,824, describes a recombinant DNA expression vector which comprises (a) a transcription unit, flanked by T-DNA border sequences, which comprises a promoter and associated amino terminal region encoding sequences and a terminator signal sequence in which the sequences are derived from one or more genes which are naturally expressed in a plant cell, and (b) an antibiotic resistance gene-encoding sequence located between the promoter and associated amino-terminal region-encoding sequence and the terminator sequence and (c) a DNA fragment containing a replicon that is functional in Agrobacterium.

PCT application 8807087, based upon U.S. patent application Ser. No. 168,109, discloses a recombinant virus expression system comprising a Heliothis polyhedrin promoter and a nucleotide sequence encoding a heterologous peptide or protein, which may have insecticidal activity.

European patent application publication number 351,924, published Jan. 24, 1990, describes a transgenic plant such as tobacco or potato comprising a lectin gene expressing a lectin within the plant foreign to the plant as found in nature. Concanavalin A, lentil (*Lens culinaris*) lectin, favin (*Vicia faba* lectin) and pea lectin are specifically disclosed. As can be seen from the data herein, *lens culinaris* lectin has been tested and found ineffective under the criteria employed here. Likewise, at least one of the lectins employed herein is disclosed as being produced in an insect cell/baculovirus expression system, as disclosed in PCT patent application 89-01037, based upon U.S. patent application Ser. No. 153778, which makes its potent insecticidal activity surprising.

European Patent Application publication number 237,676, based on U.S. application Ser. No. 837,583, describes a recombinant DNA sequence which codes for any of a) ricin A chain protein; b) the B chain portion of the ricin precursor protein; c) the A chain and B chain portions of the ricin precursor protein; or d) ricin precursor protein or polypeptide. An expression system is described as including one of the foregoing DNA sequences operably linked to a control sequence compatible with a recombinant host cell. The objective is to produce ricin toxin, precursor or fragments thereof in commercial quantities.

European Patent Application 204,590, based on U.S. patent application Ser. No. 725,368, relates to a method of genetically modifying a plant cell with a pRi tDNA promoter and a heterologous foreign structural gene, such as the lectin from *Phaseolus vulgaris*. The heterologous foreign structural gene is in position and orientation with respect to the promoter such that the structural gene is expressible in a plant cell under the control of the promoter. Expression of the *Phaseolus vulgaris* lectin is stated to be useful in improving the nutritional quality of the plant cell proteins.

DISCLOSURE OF THE INVENTION

It has now been determined that certain lectins have potent larvicidal activity when administered enterally to the larvae of insects such as European corn borer, corn rootworm, and potato leafhopper. Thus, this invention provides a method for killing susceptible insect larvae, including larvae selected from European corn borer, corn rootworm and potato leaf hopper, comprising administering enterally to the larvae a larvicidal amount of a lectin selected from the lectins obtained from:

*Artocarpus integrifolia* (jacalin)

*Bauhinia purpurea alba* (camel's foot tree) (BPA)
*Codium fragile* (CFL)
*Sambucus nigra* (elderberry) bark (EBL)
*Griffonia simplicifolia*, lectin II (GSL)
*Phytolacca americana* (PAL)
*Maclura pomifera* (osage orange) (MPL)
*Oryza sativa*
*Triticum vulgare* (Wheat germ agglutinin, WGA)
*Vicia villosa* (VVL)
*Wisteria floribunda*
*Cicer arietinum*
*Crocus vernus*
*Cystis scoparius*
*Helix aspersa*
*Helix pomatia*
*Mycoplasma gallisepticum*
*Phaseolus vulgaris* E subunit
*Urtica dioica*
Tulip spp.
*Eranthis hyemalis*
*Agropyrum repens* leaf
*Laburnum alpinum* bark (GalNAc specific lectin)
*Rhizoctonia solani*
*Listera ovata*
*Aegopodium podagraria*
*Amaranthus leucocarpus*
*Bryonia dioica*
*Limax flavus*
*Epipctis helleborine*
*Cymbidium* hybrid
*Psphopcarpus scandens* (basic lectins 1 & 2)
*Ceratobasidium cornigerum*
*Sambucus racemosa*
*Hordeum vulgare*
Sedum spp.
*Agave americana*
Dieffenbachia spp.
Salix spp.
*Crocus vernus*
*Populus canadiensis*
*Chamaecyparis lawsoniana*
*Platanus* hybrid
Berberis spp.
*Abies nobills*
*Abies pinsapo*
*Cedrus atlantica*
*Cedrus lebanoni*
*Juniperus sabina*
Picea spp. needle
Pinus spp. needle
*Sequoiadendron giganteum*
*Taxodium distichum*
*Thuya plicata*
*Agaricus bisporus* fruit bodies
*Acer pseudoplatanus* bark
*Epilobum angustifolium* leaf
*Euonymus europaeus* bark
*Pragmites australis* leaf, or a combination of such lectins. The lectin can be effectively applied to plants consumed by the larvae by spray, dust or other formulation common to the insecticidal arts. Alternatively, the lectin can be incorporated into the tissues of a susceptible plant so that in the course of infesting the plant the larvae consume larvicidal amounts of the selected lectin or lectins. One method of doing this is to incorporate the lectin in a non-phytotoxic vehicle which is adapted for systemic administration to the susceptible plants. This method is commonly employed with insecticidal materials which are designed to attack chewing insects and is well within the purview of one of ordinary skill in the art of insecticide and larvicide formulation. However, since the genes which code for these lectins can be isolated, cloned, inserted into an appropriate expression cassette, and introduced into cells of a susceptible plant species, an especially preferred embodiment of this method involves inserting into the genome of the plant a DNA sequence coding for one or more insecticidal plant lectins selected from the foregoing list in proper reading frame relative to transcription initiator and promoter sequences active in the plant. Transcription and translation of the DNA sequence under control of the plant-active regulatory sequences causes expression of the lectin protein sequence at levels which provide an insecticidal amount of the lectin in the tissues of the plant which are normally infested by the larvae. Alternatively, a dietary bait containing the selected lectin or combination of lectins can be employed, with, optionally, an added hormonal, pheromonal or other larval attractant material.

The plant is preferably a plant susceptible to infestation and damage by the larvae of one or more of European corn borer, corn rootworm and potato leafhopper. These include corn (*Zea mays*) and sorghum (*Sorghum bicolor*). However, this is not to be construed as limiting, inasmuch as these species are among the most difficult commercial crops to reliably transform and regenerate, and these insects (under other common names) also infest certain other crops. Thus the methods of this invention are readily applicable via conventional techniques to numerous plant species, if they are found to be susceptible to the plant pests listed hereinabove, including, without limitation, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersionn, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum, and Datura.

Preferred plants that are to be transformed according to the methods of this invention are cereal crops, including maize, rye, barley, wheat, sorghum, oats, millet, rice, triticale, sunflower, alfalfa, rapeseed and soybean, fiber crops, such as cotton, and vegetable crops, including onion, pepper, tomato, carrot, crucifer (cabbage, broccoli, cauliflower), eggplant, spinach, potato and lettuce.

The DNA sequence which when expressed imparts insecticidal activity is a structural gene which codes for one of the selected plant lectins described herein. It has been found that, although numerous lectins are known to biological science and a few of these have now been found to exhibit some insecticidal activity, only those described herein have been found to have sufficient insecticidal (larvicidal) activity to be operative in a plant cell expression system. That is, while other lectins have some larvicidal activity at high concentrations in pure form, plant cell expression at such high concentrations is either not possible in a living plant cell system, or is not likely while preserving the commercially useful characteristics of the plant in terms of production of oils, starches, fibers, or other materials. In addition, lectins which are active against some insects are inactive against others. For example, wheat germ agglutinin, one of the preferred lectins herein, is very toxic to the larvae of the European corn borer but relatively nontoxic to tobacco budworm and Southern Corn Rootworm. Soybean lectin, Concanavalin A and peanut lectin have not shown significant activity against any insects tested to date. The preferred lectins in the practice of this invention are jacalin, *Bauhinia purpurea alba* lectin, *Codium fragile* lectin, *Griffonia simplicifolia* II lectin, *Phytolacca americana* lectin, *Maclura pomifera* lectin, *Triticum vulgate* lectin (Wheat germ agglutinin), *Phaseolus vulgaris* lectin E subunit, *Crocus vernus* lectin, *Eranthis hyemalis* lectin, and *Vicia villosa* lectin. In general, since the object of the invention is to confer resistance to an insect to which the plant is susceptible, the selected lectin will not be native to the plant, i.e., the lectin will come from a species other than the plant being transformed. However, in species which produce larvicidal lectins but in lower than larvicidal amounts, it may be preferable to insert a gene for the native lectin under strong constitutive promoter control to cause overproduction of the lectin, thus achieving larvicidal levels and conferring effective insect resistance. Alternatively, where a plant produces a native larvicidal lectin but the lectin is not produced in or not distributed to tissues which are normally infested by the larvae, a tissue specific promoter can be used to provide localized expression or overproduction of the lectin. A tissue specific promoter can be used in any instance where it may be desirable to localize production of the lectin to an infested tissue or to a tissue which is efficient in production of the lectin.

The DNA sequences which code for the lectins of this invention can be obtained by conventional techniques. *Ricinus communis* agglutinin, for example, although not claimed herein, has been sequenced to the extent that DNA probes can be constructed to locate the native gene in the *Ricinus communis* genome, and the gene can then be removed by use of appropriate restriction enzymes and spliced into a selected plant expression cassette. Alternatively, the lectin can be sequenced in its entirety using known methods, and synthetic DNA sequences can then be prepared which code for the appropriate sequence of amino acids, and this synthetic sequence can be inserted into an appropriate plant expression cassette. These techniques are applicable to each of the lectins identified herein as useful in this invention.

Figure 1:
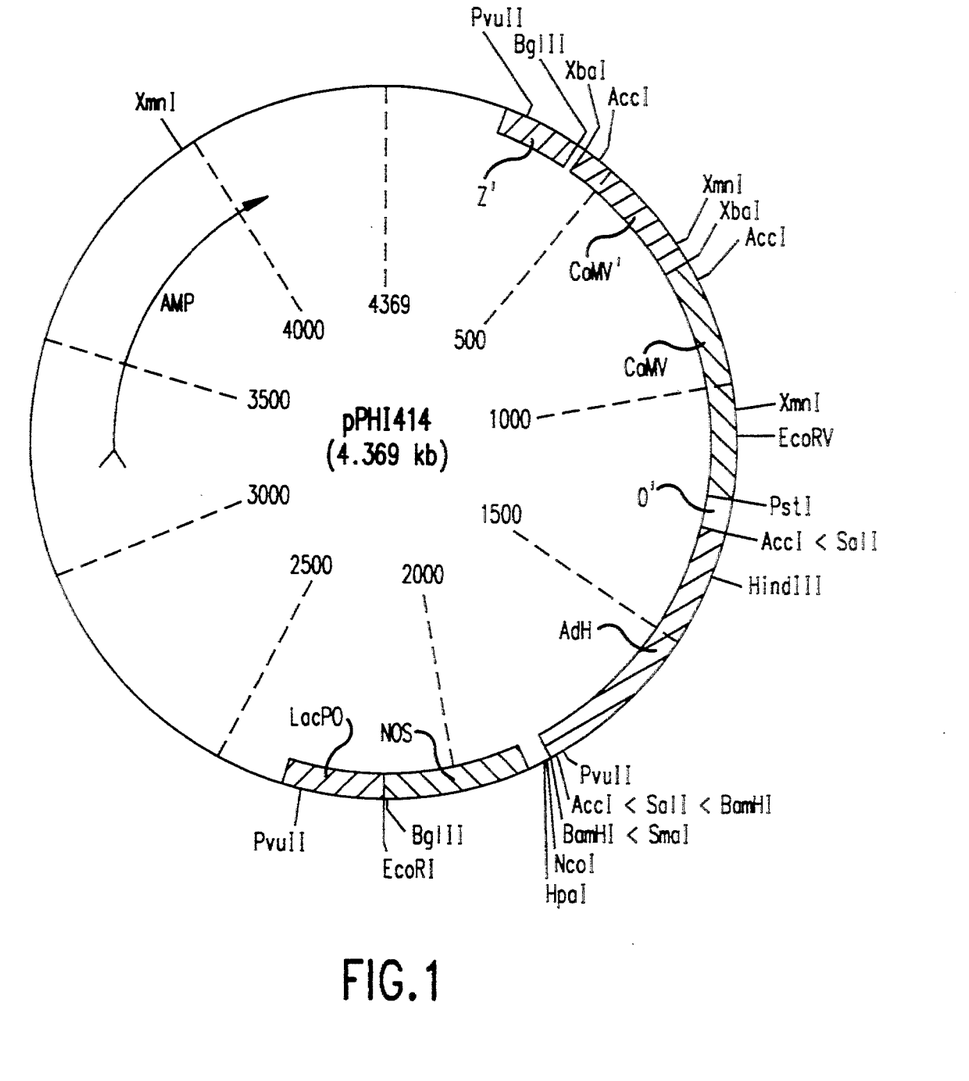
FIG. 1 illustrates the gene map of plasmid pPHI414 which is useful as an expression cassette for lectin structural genes.
Figure 2:
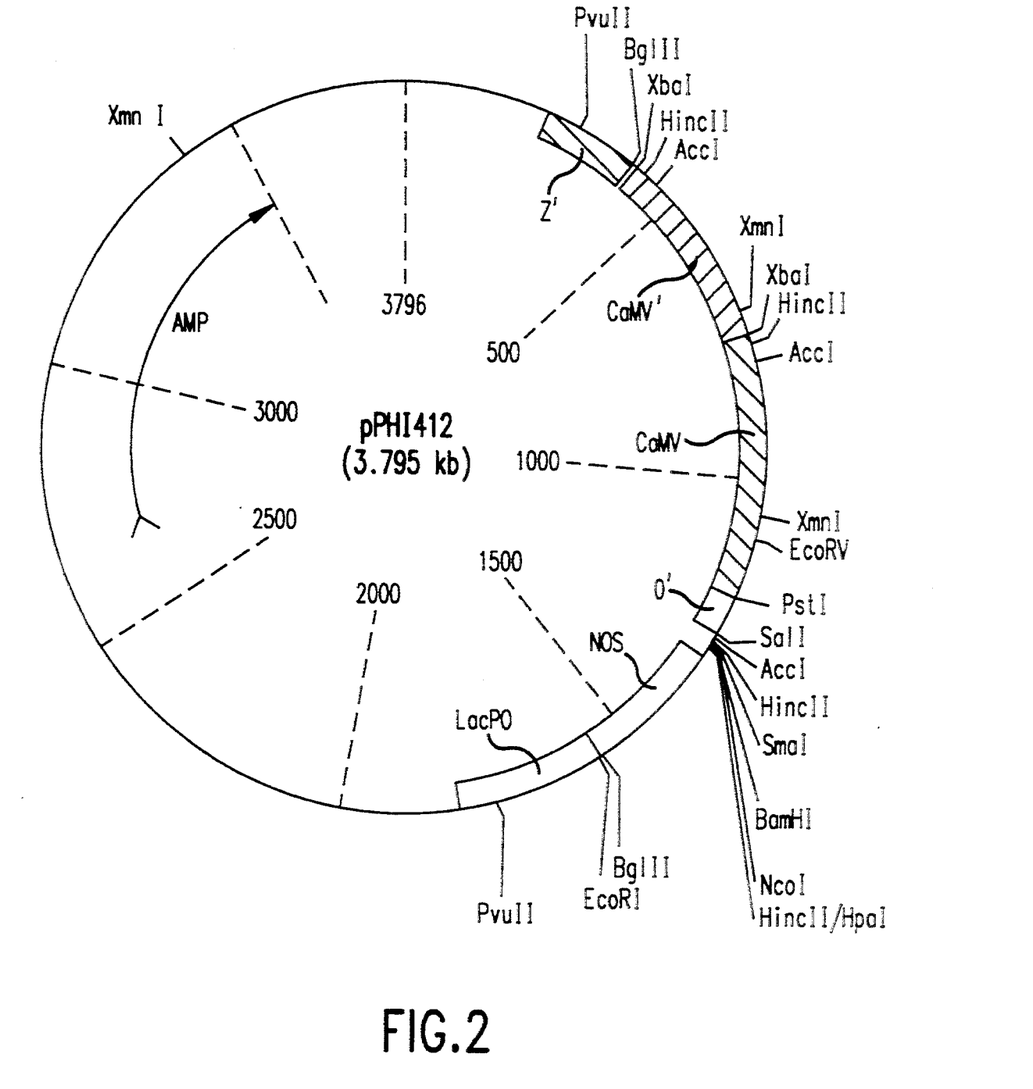
FIG. 2 illustrates the gene map of plasmid pPHI412 which is also useful as an expression cassette for lectin structural genes.
Figure 3:
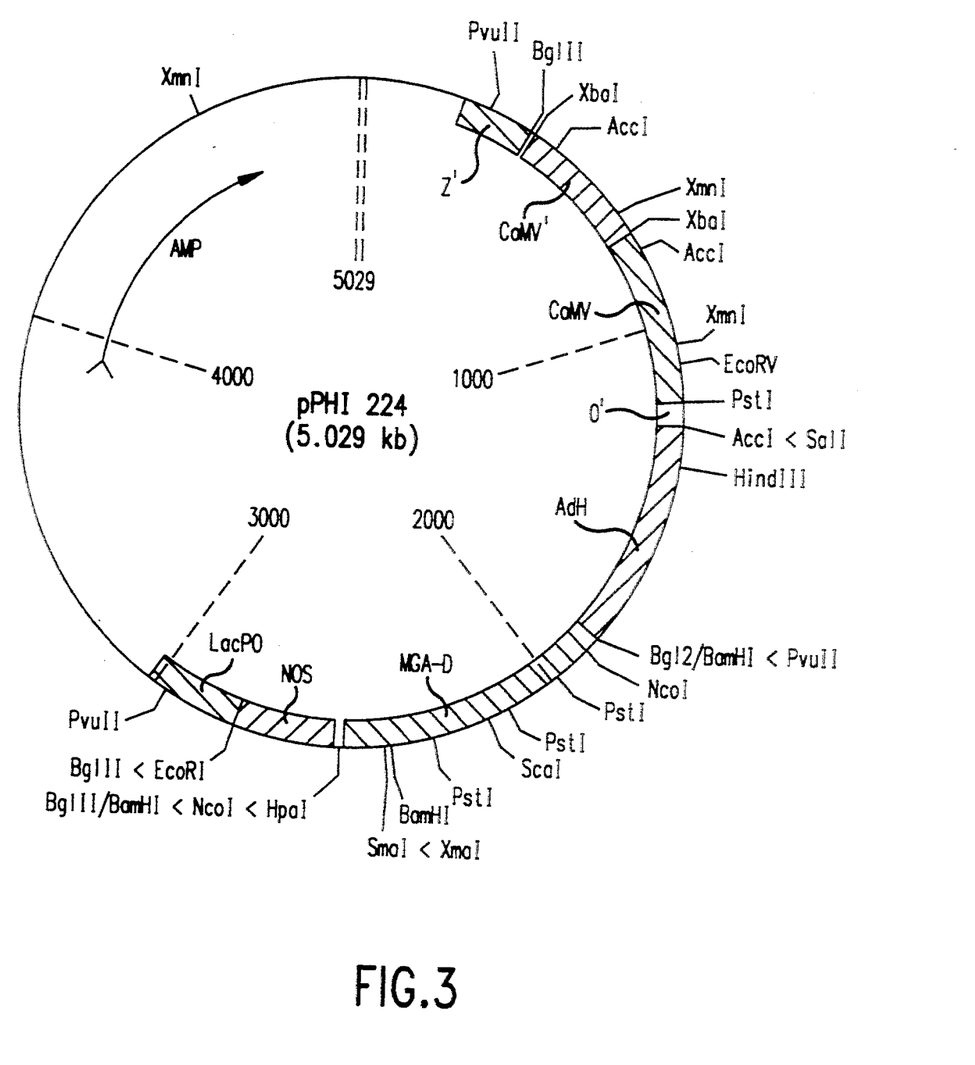
FIG. 3 illustrates the gene map of plasmid pPHI224 which is a specific expression cassette for containing the structural gene for the lectin Wheat Germ Agglutinin.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Iowa. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as selectable markers to identify and separate transformed cells. Preferred selection agents include kanamycin, chlorosulfuron, phosphonothricin, hygromycin and methotrexate, and preferred markers are genes conferring resistance to these compounds. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs and CaMV promoters.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al, *J. Molecular and App. Gen.*, 1: 483–498 (1982)), and the promoter of the cholorophyll a-b binding protein. These two promoters are known to be light-induced, in eukaryotic plant cells (see, for example, *Genetic Engineering of Plants, An Agricultural Perspective*, A. Cashmore, Pelham, New York, 1983, pp. 29-38, G. Coruzzi et al., *J. Biol. Chem.*, 258:1399 (1983), and P. Dunsmuir, et al., *J. Molecular and App. Gen.*, 2:285 (1983)).

The expression cassette comprising the structural gene for the lectin of interest operably linked to the desired control sequences can be ligated into a suitable cloning vector. In general, plasmid or vital (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention.

The isolated cloning vector will then be introduced into the plant cell using any convenient technique, including electropotation (in protoplasts), retroviruses, bombardment, and microinjection, into cells from monocotyledonous or dicotyledonous plants, in cell or tissue culture, to provide transformed plant cells containing as foreign DNA at least one copy of the DNA sequence of the plant expression cassette. Preferably, the monocotyledonous species will be selected from maize, sorghum, wheat and rice, and the dicotyledonous species will be selected from soybean, sunflower, cotton, rapeseed (either edible or industrial), alfalfa, tobacco, and Solanaceae such as potato and tomato. Using known techniques, protoplasts can be regenerated and cell or tissue culture can be regenerated to form whole fertile plants which carry and express the desired gene for the selected lectin. Accordingly, a highly preferred embodiment of the present invention is a transformed maize plant, the cells of which contain as foreign DNA at least one copy of the DNA sequence of an expression cassette of this invention.

This invention also provides methods of imparting resistance to insects selected from European corn borer, corn rootworm, and potato leafhopper to plants of a susceptible taxon, comprising the steps of:

a) culturing cells or tissues from at least one plant from the taxon, b) introducing into the cells of the cell or tissue culture at least one copy of an expression cassette comprising a structural gene for a lectin selected from the lectins obtained from:

*Artocarpus integrifolia* (jacalin)
*Bauhinia purpurea alba* (camel's foot tree) (BPA)
*Codium fragile* (CFL)
*Sambucus nigra* (elderberry) bark (EBL)
*Griffonia simplicifolia,* lectin II (GSL)
*Phytolacca americana* (PAL)
*Maclura pomifera* (osage orange) (MPL)
*Oryza sativa*
*Triticum vulgare* (Wheat germ agglutinin, WGA)
*Vicia villosa* (VVL)
*Wisteria floribunda*
*Cicer arietinum*
*Crocus remus*
*Cystis scoparius*
*Helix aspersa*
*Helix pomatia*
*Mycoplasma gallisepticum*
*Phaseolus vulgaris* E subunit
*Urtica dioica*
Tulip spp.
*Eranthis hyemalis*
*Agropyrum repens* leaf
*Laburnum alpinum* bark (GalNAc specific lectin)
*Rhizoctonia solani*
*Listera ovata*
*Aegopodium podagraria*
*Amaranthus leucocarpus*
*Bryonia dioica*
*Limax flavus*
*Epictis helleborine*
Cymbidium hybrid
*Pshopcarpus scandens* (basic lectins 1 & 2)
*Ceratobasidium cornigerum*
*Sambucus racemosa*
*Hordeum vulgate*
Sedum spp.
*Agave americana*
Dieffenbachia spp.
Salix spp.
*Crocus vernus*
*populus canadiensis*
*Chamaecyparis lawsoniana*
Platanus hybrid
Berberis spp.
*Abies nobilis*
*Abies pinsapo*
*Cedrus atlantica*
*Cedrus lebanoni*
*Juniperus sabina*
Picea spp. needle
Pinus spp. needle
*Sequoiadendron giganteum*
*Taxodium distichum*
*Thuya plicata*
*Agaricus bisporus* fruit bodies
*Acer pseudoplatanus* bark
*Epilobum angustifolium* leaf
*Euonymus europaeus* bark
*Pragmites australis* leaf, or a combination of such lectins operably linked to plant regulatory sequences which cause the expression of the lectin structural gene in the cells, and c) regenerating insect-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the lectin structural gene and associated regulatory sequences via crossing and backcrossing. Such intermediate methods will comprise the further steps of a) sexually crossing the insect-resistant plant with a plant from the insect-susceptible taxon;

b) recovering reproductive material from the progeny of the cross; and c) growing insect-resistant plants from the reproductive material. Where desirable or necessary, the agronomic characteristics of the susceptible taxon can be substantially preserved by expanding this method to include the further steps of repetitively:

a) backcrossing the insect-resistant progeny with insect-susceptible plants from the susceptible taxon; and b) selecting for expression of insect resistance (or an associated marker gene) among the progeny of the backcross, until the desired percentage of the characteristics of the susceptible taxon are present in the progeny along with the gene imparting insect resistance.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens,* which can then be used to transfer the vector into susceptible plant cells, primarily from dicotyledonous species. Thus, this invention provides a method for imparting insect resistance in *Agrobacterium tumefaciens*-susceptible dicotyledonous plants in which the expression cassette is introduced into the cells by infecting the cells with *Agrobacterium tumefaciens,* a plasmid of which has been modified to include a plant expression cassette of this invention.

Finally, it has now been determined that susceptibility to lectins in European corn borer is determined by the lectin binding affinity of a single 22 kd protein from the larval peritrophic membrane. Thus, this protein can be a target for any other compound or protein which binds to it strongly and preferentially. In view of this, the invention now also provides a methods and compositions for killing European corn borer as described hereinbefore, but in which in lieu of a lectin there is employed a compound which binds to the 22 kd protein from the European corn borer peritrophic membrane. Such compounds can desirably include the lectins described herein, or can be an antibody or other protein with high binding affinity for the 22 kd protein from the peritrophic membrane of ECB.

In the traditional method of preparing a heterologous antiserum, the antigen (in this instance the 22 kd protein from the ECB peritrophic membrane) is injected into an immunologically competent animal. Numerous populations of lymphocytes arise within the animal's spleen which make antibodies which bind to a single antigenic determinant on the antigen. The animal's serum can then be withdrawn and the antibodies isolated and purified.

In the more recent method of producing monoclonal antibodies, cell fusion techniques are used to construct hybridoma cell lines. Spleen lymphocytes from am animal immunized with the antigen are immortalized by fusion with mouse myeloma cells. Once the hybridoma cells are constructed they are cloned and grown up so that groups of cells are obtained, each of which is producing only a single monoclonal antibody. Hybridomas are screened for antibody production using methods such as enzyme linked immunosorbant assays. The antigen (in this invention the 22 kd protein from the ECB peritrophic membrane) is bound to a support such as a well in a microtiter plate. A sample of the culture medium is placed in the well. Medium from a hybridoma culture which is producing antibody will react with the antigen on the well. After washing to remove unbound antibody, a second antibody which reacts with another antibody such as a murine antibody is added. This antibody binds to the hybridoma antibody already bound to its antigen. The second antibody is tagged with an enzyme such as peroxidase or alkaline phosphatase. In the presence of an appropriate substrate the enzyme produces a colored reaction product which can be scored visually or electromechanically. Antibody-positive hybridomas are cloned to isolate cells producing antibody, which are isolated to prevent overgrowth by nonproducing cells.

Once the foregoing steps have been performed, the antibody can be obtained from the hybridoma cells in significant quantities and purified, and its structure, including its amino acid sequence, can be identified.

The polyclonal or monoclonal antibodies to the 22 kd protein of the ECB peritrophic membrane can be used directly in the manner of this invention as compounds which kill ECB larvae when administered enterally to the larvae as described herein, such as by use as a larvicidal powder or spray.

Alternatively, the antibodies, especially the monoclonal antibodies, can be sequenced and the sequence information used to construct synthetic genes which code substantially solely for the antibody. Or, the antibody can be partially sequenced to identify oligonucleotides which can then be used as probes or polymerase chain reaction (PCR) primers to isolate from the hybridoma cells the naturally occurring gene which codes substantially solely for the antibody. The natural or synthetic gene sequence can then be incorporated into a suitable expression cassette as described herein and introduced into a target plant species, such as corn, by any effective transformation method, such as microparticle bombardment. Plants so transformed will express the antibody or other protein which binds strongly to the 22 kd protein from the ECB larval peritrophic membrane, and ECB larvae which feed on the transformed plants will be killed or have their growth significantly impaired.

In like manner, the protein identification method disclosed herein can be used with any of the lectins taught herein to be larvicidally active, and any of the insect species taught herein to be susceptible, as a rapid screening method to identify in those other insect species, including corn rootworm, whitefly and potato leafhopper, the peritrophic membrane protein which is bound by the effective lectins. Using that information, the protein and antibody techniques well known to the art and described above in general fashion can be employed to create larvicidal compositions and transgenic plants which are resistant to infestation by larvae of those other species.

A significant advantage of this method is that since insecticide resistance generally arises through the occurrence of spontaneous mutations in the gene which codes for the protein which is the target of the insecticide, by using the method of this invention the target protein can be identified in advance and mutations can be tracked. When a mutation occurs which gives rise to tolerance in the target insect larvae, the other antibodies prepared from the protein can be screened for activity and an antibody which retains activity can be used. Alternatively, the mutated protein or mutein can be used again as an antigen and a new series of antibodies can be prepared which can again be used in the manner of this invention. Thus, a plant species or plant variety can be kept insect-resistant for long periods through repeated use of the methods of this invention, without the need for resort to increasing levels or treatment rates of larvicidally active materials and without resort to new larvicidal chemistries which may be less environmentally desirable.

The following description further exemplifies the compositions of this invention and the methods of making and using them. However, it will be understood that other methods, known by those of ordinary skill in the art to be equivalent, can also be employed.

EXAMPLE 1

Insect Susceptibility to Lectins

Since one of the primary routes of administration of insecticidal substances to insect pests is via the digestive tract, the susceptibility of selected insect larvae to an assortment lectins administered in the diet was evaluated. European cornborers (ECB), *Ostrinia nubilalis* (Hubner), Southern corn rootworm (SCRW), *Diabrotica undecimpunctata howardi* Barber, were used to screen lectins for anti-insect activity. In all bioassays, ECB and SCRW larvae were reared in tissue culture tray cells (4×6 cells/tray) that contained approximately 1.5 g of Stoneville artificial media (pH 5.6). Three treatments plus one control, each composed of one row of six cells, were infested with 2 neonate larvae per cell. A mylar film was adhered to the top of each tray after infestation to prevent escape of the larvae. The mylar was then punctured with insect pins (size 0) and attached to a cork stopper to provide adequate air flow.

Bioassays of Insect Susceptibility to Enterally Administered Lectins

A 2% solution of each lectin was prepared in 0.1M PBS buffer (pH 7.8). Seventy-five μl were then applied topically to the surface of the media in each cell. After the solution had dried, the cell was infested with two neonate larvae. The control treatment consisted of a 75 μl application of buffer only per cell. Larval weights and mortalities were recorded after seven days solution and compared to those of the control treatment. Lectins that inhibited larval growth by 50% or produced 25% mortality when compared to the control treatment were tested again. Lectins that continued to display anti-insect activity were then tested using a bioassay in which the lectin was incorporated in the diet.

RESULTS

Results are shown in Tables 1 and 2. One hundred twenty-seven lectins, differing in carbohydrate-binding specificity, were examined for anti-insect activity against neonate ECB and SCR larvae by these bioassays, and twelve were screened for activity against potato leafhopper. Eight lectins showed positive results that caused either 25% mortality and/or a 50% weight reduction in treated larvae compared to control larvae. These eight lectins were *Artocarpus integrifolia* lectin (jacalin), *Bauhinia purpurea alba* (BPA) lectin, *Codium fragile* lectin (CFL), *Griffonia simplicifolia* (GSII), *Phytolacca americana* lectin (PAL), *Maclura pomifera* lectin (MPL), *Triticum vulgare* lectin (Wheat germ agglutinin, WGA), and *Vicia villosa* lectin (VVL). Two of these materials were active against ECB larvae, while seven had activity against SCR larvae.

WGA and BPA were the only lectins of the 127 tested which displayed antilarval effectiveness on neonate ECB larvae. At the 2% test level of lectin applied topically to the medium, 100% mortality occurred within seven days in all treated cells (Table 1). WGA maintained its anti-insect activity down to the 0.1% level by inhibiting weight gain by 50% (details of data not shown). None of the other lectins tested had anti-insect activity against ECB as determined by the preset levels. The addition of 2% casein topically to the media surface did not affect larval weights, indicating that other proteins do not interfere with the insecticidal activity of the lectin.

TABLE 1

Lectins from a variety of plant and animal sources as indicated below were screened for anti-insect activity against neonate European Cornborer and Southern Corn rootworm larvae[1].

| Species | Common Name | M.W. (Kd) | Anti-Insect |
|---|---|---|---|
| *Artocarpus integrifolia* | | 40 | Yes |
| *Arachis hypogaea* | | 110 | No |
| *Bauhinia purpurea alba* | | 195 | Yes |
| *Canavalia ensiformis* | | 104 | No |
| *Codium fragile* | | 60 | Yes |
| *Datura stramonium* | | 86 | No |
| *Dolichos biflorus* | | 120 | No |
| *Erythrina cristagalli* | | 54 | No |
| *Sambucus nigra* bark | | 150 | Yes |
| *Glycine max* | | 120 | No |
| *Griffonia simplicifolia:* | | | |
| I | | 115 | No |
| II | | 115 | Yes |
| *Lens culinaris* | | 49 | No |
| *Limulus polyphemus* | | 400 | No |
| *Lotus tetrabonolobus* | | 56-112 | No |
| *Lycopersicon esculentum* | | 100 | No |
| *Maclura pomifera* | | 40-43 | Yes |
| *Naja mocambique* | | | No |
| *Oryza sativa* | | | Yes |
| *Perseau americana* | | | No |
| *Phytolacca americana* | | 32 | Yes |
| *Pisum sativum* | | 46 | No |
| *Phaseolus cocineus* | | 112 | No |
| *Phaseolus limensis* | | 247(II) 247(III) | No |
| *Phaseolus vulgaris* E | | 125 | No |
| *Phaseolus vulgaris* L | | 125 | No |
| *Ricinus communis* | | 120 | No |
| *Sambucus nigra* | | 140 | No |
| *Solanum tuberosum* | | 100 | No |
| *Sophora japonica* | | 133 | No |
| *Triticum vulgare* | | 36 | Yes |
| *Ulex europaeus* I | | 170 | No |
| *Ulex europaeus* II | | 170 | No |
| *Vicia villosa* | | 139 | Yes |
| *Viscum album* | | 115 | No |
| *Wistaria floribunda* | | 68 | No |
| Semi-purified Lectins | | | |
| Sopharo Leaf doublet | | | No |
| Sopharo Bark Lectin II | | | No |
| Sopharo Bark Lectin III | | | No |
| Sopharo Bark Lectin V | | | No |
| Sopharo Leaf Lectin I | | | No |
| Sopharo Leaf Lectin II | | | No |
| Phaseolus Tepary | | | No |
| Sparticum Spanish bloom | | | No |
| *Cicer arietinum* | Chick pea | 44 | Yes |
| *Cytisus scoparius* | Scotch broom | | Yes |
| *Helix aspersa* | Garden snail | 79 | Yes |
| *Helix pomatia* | Edible snail | 79 | Yes |
| *Mycoplasma gallisepticum* | | | Yes |
| *Ptilota plumosa* | Red marine algae | 65;170 | No |
| *Robinia pseudoacacia* | False acacia black locust | 100 | No |
| *Urtica dioica* | Stinging nettle | 8.5 | Yes |
| *Agaricus bisporus* | Mushroom | | No |
| | Tulip lectin | | Yes |
| *Momordica charantia* | Bitter pear melon | | No |
| *Eranthis hyemalis* | | | Yes |
| *Agropyrum repens* leaf lectin | | | Yes |
| *Laburnum alpinum* bark lectin | GalNAc specific | | Yes |
| *Rhizoctonia solani* AG1C | | | Yes |
| *Listera ovata* | | | Yes |
| *Aegopodium podagraria* | | | Yes |
| *Amaranthus leucocarpus* | | | Yes |
| *Bryonia dioica* | | | Yes |
| *Sambucus racemosa* | | | No |
| *Sambucus ebulus* | | | No |
| *Chelidonium majus* | | | No |
| *Laburnum alpinum* fucose specific | | | No |
| *Robinia pseudoacacia* Bark lectin | | | No |

TABLE 1-continued

Lectins from a variety of plant and animal sources as indicated below were screened for anti-insect activity against neonate European Cornborer and Southern Corn rootworm larvae[1].

| Species | Common Name | M.W. (Kd) | Anti-Insect |
|---|---|---|---|
| *Maacka amurensis* Bark lectin | | | No |
| *Robinia pseudoacacia* Bark lectin Special isolectin | | | No |
| *Robinia pseudoacacia* 3 | | | No |
| *Robinia pseudoacacia* 1 | | | No |
| *Limax flavus* | Slug | | Yes |
| *Epipctis helleborine* | | | Yes |
| *Cymbidium* hybrid | | | Yes |
| *Arum maculatum* | | | No |
| *Psphopcarpus scandens* Basic lectin 1 | | | Yes |
| *Psphopcarpus scandens* Basic lectin 1 & 2 | | | Yes |
| Chitin binding protein from *Bryonia dioica* | | | Yes |
| *Ceratobasidium cornigerum* | | | Yes |
| *Rhizoctonia solani* anastomosis group AG 1A | | | Yes |
| *Rhizoctonia solani* anastomosis group AG 2-1 | | | Yes |
| *Rhizoctonia solani* anastomosis group AG 2-2 | | | Yes |
| *Rhizoctonia solani* anastomosis group AG 4 | | | Yes |
| *Pragmites australis* leaf lectin | | | Yes |
| *Iris* hybrid | | | No |
| *Galega officinalis* | | | No |
| *Sambucus nigra* bark lectin II | | | No |
| *Sambucus racemosa* bark lectin II | | | No |
| *Hordeum vulgare* | | | Yes |
| *Solanum dulcamara* | | | No |
| *Sedum* spp. | | | Yes |
| *Agave americana* | | | Yes |
| *Dieffenbachia* spp. | | | Yes |
| Salix | | | Yes |
| *Crocus vernus* | | | Yes |
| *Pinus nigra* | | | Yes |
| *Populus x canadiensis* | | | Yes |
| *Chamaecyparis lawsoniana* | | | Yes |
| Kiwi | | | Yes |
| *Platanus* hybrid | | | Yes |
| Cranberry | | | Yes |
| Berberis | | | Yes |
| *Allium ursinum* | | | No |
| *Allium sativum* | | | No |
| *Galanthus nivalis* | | | No |
| *Hippeastrum* hybrid | | | No |
| *Narcissus pseudonarcissus* | | | No |
| *Abies nobilis* | | | Yes |
| *Abies pinsapo* | | | Yes |
| *Cedrus atlantica* | | | Yes |
| *Cedrus lebanoni* | | | Yes |
| *Gingko biloba* | | | No |
| *Juniperus sabina* | | | Yes |
| *Picea abies* | | | Yes |
| *Picea banksiana* | | | Yes |
| *Picea excelsa* | | | Yes |
| *Picea jezioensis* | | | Yes |
| *Picea marriana* | | | Yes |
| *Picea omorica* | | | Yes |
| *Picea orientalis* | | | Yes |
| *Picea pungens* | | | Yes |
| *Picea sitchensis* | | | Yes |
| *Picea torano* | | | Yes |
| *Pinus avacantha* | | | Yes |
| *Pinus flexilis* | | | Yes |
| *Pinus nigra* | | | Yes |
| *Pinus ponderosa* | | | Yes |
| *Pinus rigida* | | | Yes |
| *Pinus sylvestris* | | | Yes |
| *Sequioadendron giganteum* | | | Yes |
| *Taxodium distichum* | | | Yes |
| *Thuya occidentalis* | | | No |
| *Thuya plicata* | | | Yes |
| *Torreya californica* | | | No |
| *Agaricus bisporus* fruit bodies | | | Yes |
| *Acer pseudoplatanus* bark | | | Yes |
| *Epilobium angustifolium* leaf | | | Yes |
| *Musa* leaf | | | No |
| *Musa* fruit | | | No |
| *Euonymus europaeus* bark | | | Yes |

[1]Anti-Insect activity was predetermined to be 25% mortality and/or 40% weight loss after a 7-day, 2% topical application to the medium in either insect when compared to the control larvae.

TABLE 2

Effect of anti-insect lectins topically applied to medium on mortality and weight of neonate European corn borer and Southern corn rootworm larvae[1]

| Lectin | Insect[2] | Weight[3] | % Weight[4] Loss | %[5] Mortality | n[6] |
|---|---|---|---|---|---|
| Specificity: N-acetylglucosamine | | | | | |
| GSL II | ECB | 5.0 ± 0.4 | 15 | 0 | 6 |
| | SCR | 0.3 ± 0.1* | 80 | 15 | 12 |
| PAL | ECB | 5.8 ± 0.6 | 0 | 0 | 6 |
| | SCR | 1.4 ± 0.4 | 0 | 35 | 12 |
| WGA | ECB | N.A. | N.A. | 100 | 18 |
| | SCR | 0.6 ± 0.1* | 58 | 10 | 36 |
| *Urotica dioica* | ECB | 4.5 ± 0.4 | — | — | 3 |
| | SCR | 0.2 ± 0.1 | 90 | 45 | 11 |
| *Oryza sativa* | ECB | 1.6 ± 2.5 | 85 | 33 | 6 |
| | SCR | 0.6 ± 0.5 | 75 | 0 | 6 |
| *Agropyrum repens* leaf | ECB | 0.0* | 100 | 67 | 6 |
| | SCR | 0.5 ± 0.3* | 85 | 0 | 5 |
| *Bryonia dioica* chitin binding protein | ECB | 7.8 ± 2.0 | 0 | 0 | 3 |
| | SCR | 1.9 ± 0.4* | 45 | 0 | 6 |
| *Pragmites australis* leaf | ECB | 4.9 ± 0.5* | 40 | 0 | 6 |
| | SCR | 2.9 ± 0.5 | 20 | 0 | 3 |
| Specificity: N—acetylgalactosamine/galactose | | | | | |
| jacalin | ECB | 5.8 ± 0.6 | 0 | 0 | 6 |
| | SCR | 0.4 ± 0.1* | 70 | 0 | 36 |
| BPA lectin | ECB | N.A. | N.A. | 100 | 12 |
| | SCR | 0.9 ± 0.2* | 35 | 10 | 28 |
| CFL | ECB | 5.5 ± 0.5 | 0 | 0 | 6 |
| | SCR | 0.2 ± 0.1* | 85 | 35 | 9 |
| MPL | ECB | 5.9 ± 0.6 | 0 | 0 | 0 |
| | SCR | 0.2 ± 0.1* | 85 | 0 | 12 |
| VVL | ECB | 6.4 ± 0.5 | 0 | 0 | 6 |
| | SCR | 0.5 ± 0.1* | 65 | 10 | 9 |
| *Cytisus scoparius* | ECB | 3.8 ± 0.5 | — | — | 3 |

TABLE 2-continued

Effect of anti-insect lectins topically applied to medium on mortality and weight of neonate European corn borer and Southern corn rootworm larvae[1]

| Lectin | Insect[2] | Weight[3] | % Weight[4] Loss | %[5] Mortality | n[6] |
|---|---|---|---|---|---|
| | SCR | 0.01 ± 0.01 | 95 | 60 | 3 |
| Helix aspersa | ECB | 4.5 ± 0.5 | — | — | 6 |
| | SCR | 0.3 | 85 | 92 | 15 |
| Helix pomatia | ECB | — | — | — | — |
| | SCR | 0.3 ± 0.1 | 85 | 60 | 12 |
| Crocus vernus | ECB | 0.5 ± 2.6 | 95 | 50 | 6 |
| | SCR | 0.1 ± 0.3 | 95 | 0 | 6 |
| Laburnum alpinum bark | ECB | 3.2 ± 0.6* | 50 | 0 | 6 |
| | SCR | 1.4 ± 0.3* | 55 | 40 | 5 |
| GalNAc specific | | | | | |
| Psphopcarpus scandens B1 | ECB | 6.5 ± 0.5* | 15 | 0 | 6 |
| | SCR | 1.9 ± 0.6 | 40 | | 3 |
| Psphopcarpus scandens B1 & B2 | ECB | 4.0 ± 0.7* | 50 | 0 | 6 |
| | SCR | 1.3 ± 0.2 | 60 | | 3 |
| Specificity: Other | | | | | |
| Cicer arietinum | ECB | 3.5 ± 0.5 | — | — | 6 |
| | SCR | 0.1 ± 0.1 | 95 | 0 | 6 |
| Mycoplasma gallisepticum | ECB | 3.5 ± 0.8 | — | — | 3 |
| | SCR | 0.1 ± 0.1 | 95 | 60 | 3 |
| Aegopodium podagraria | ECB | 9.3 ± 1.7 | 0 | 0 | 3 |
| | SCR | 1.9 ± 0.2* | 40 | 17 | 6 |
| Amaranthus leucocarpus | ECB | 7.7 ± 0.3 | 0 | 0 | 3 |
| | SCR | 0.5 ± 0.2* | 85 | 0 | 6 |
| Bryonia dioica | ECB | 5.9 ± 1.5 | 20 | 0 | 3 |
| | SCR | 2.0 ± 0.2* | 40 | 17 | 6 |
| Ceratobasidium cornigerum | ECB | 8.0 ± 2.0 | 0 | 0 | 3 |
| | SCR | 0.6 ± 0.1 | 80 | 0 | 3 |
| Cymbidium hybrid | ECB | 13.0 ± 2.0 | 0 | 0 | 3 |
| | SCR | 0.4 ± 0.4 | 40 | 33 | 6 |
| Epipctis helleborine | ECB | 7.7 ± 1.0 | — | — | 3 |
| | SCR | 1.7 ± 0.3 | 50 | 0 | 6 |
| Eranthis hyemalis | ECB | 4.2 ± 0.7* | 35 | 17 | 6 |
| | SCR | — | — | 100 | 6 |
| Limax flavus | ECB | not tested | | | |
| | SCR | — | — | 100 | 2 |
| Listera ovata | ECB | 7.3 ± 0.6 | 0 | 0 | 3 |
| | SCR | 1.3 ± 0.3* | 60 | 33 | 6 |
| Rhizoctonia solani group AG 1C | ECB | 6.1 ± 0.6 | 20 | 0 | 3 |
| | SCR | 0.3 ± 0.4* | 90 | 33 | 6 |
| Rhizoctonia solani anastomosis group AG 1A | ECB | 11.5 ± 1.5 | 0 | 0 | 3 |
| | SCR | 1.8 ± 0.4* | 50 | 0 | 6 |
| Rhizoctonia solani anastomosis group AG 2-1 | ECB | 8.8 ± 1.5 | 0 | 0 | 3 |
| | SCR | 1.6 ± 0.4 | 55 | 0 | 6 |
| Rhizoctonia solani anastomosis group AG 2-2 | ECB | 8.1 ± 1.3 | 0 | 0 | 3 |
| | SCR | 0.9 ± 0.2 | 75 | 0 | 3 |
| Rhizoctonia solani anastomosis group AG 4 | ECB | 7.6 ± 0.9 | 0 | 0 | 3 |
| | SCR | 1.7 ± 0.4 | 50 | 0 | 6 |
| Tulip lectin | ECB | 3.6 ± 0.5* | 45 | 0 | 6 |
| | SCR | 0.2 ± 0.3* | 95 | 33 | 6 |
| Dieffenbachia sp | ECB | 2.8 ± 2.6 | 70 | 0 | 6 |
| | SCR | 1.7 ± 0.5 | 35 | 0 | 6 |
| Sedum spp. | ECB | no effect | | | |
| | SCR | 0.6 ± 0.3 | 75 | 0 | 6 |
| Salix caprea | ECB | 7.4 ± 2.0 | 30 | 0 | 6 |
| | SCR | 0.5 ± 0.3 | 80 | 0 | 6 |
| Pinus nigra | ECB | 6.1 ± 2.5 | 35 | 0 | 6 |
| | SCR | 0.7 ± 0.3 | 75 | 0 | 6 |
| Populus x canadiensis | ECB | no effect | | | |
| | SCR | 0.7 ± 0.3 | 75 | 0 | 6 |
| Chamaecyparis lawsoniana | ECB | no effect | | | |
| | SCR | 0.7 ± 0.3 | 75 | 0 | 6 |
| Kiwi fruit | ECB | no effect | | | |
| | SCR | 0.3 ± 0.3 | 90 | 0 | 6 |
| Platanus hybrid | ECB | no effect | | | |
| | SCR | 0.5 ± 0.3 | 80 | 0 | 6 |
| Cranberry fruit | ECB | no effect | | | |
| | SCR | 0.5 ± 0.3 | 80 | 0 | 6 |
| Berberis spp. | ECB | no effect | | | |
| | SCR | 0.4 ± 0.3 | 85 | 0 | 6 |
| Hordeum vulgare | ECB | 4.5 ± 1.0 | 85 | 0 | 3 |
| | SCR | not tested | | | |
| Epilobium angustifolium | ECB | 2.2 ± 0.6 | 60 | 0 | 6 |
| | SCR | 0.7 ± 0.2 | 70 | 0 | 6 |
| Lectins from the needles of the following gymnosperms: | | | | | |
| Abies nobilis | ECB | 3.6 ± 1.0 | 50 | 0 | 6 |
| | SCR | 0.7 ± 0.1 | 80 | 0 | 6 |
| Abies pinsapo | ECB | 2.5 ± 0.7 | 65 | 0 | 6 |

TABLE 2-continued

Effect of anti-insect lectins topically applied to medium on mortality and weight of neonate European corn borer and Southern corn rootworm larvae[1]

| Lectin | Insect[2] | Weight[3] | % Weight[4] Loss | %[5] Mortality | n[6] |
|---|---|---|---|---|---|
| Abies procera | SCR | 0.7 ± 0.1 | 80 | 0 | 6 |
|  | ECB | 1.7 ± 0.6 | 75 | 0 | 6 |
| Cedrus atlantica | SCR | 0.6 ± 0.1 | 80 | 0 | 6 |
|  | ECB | no effect |  |  |  |
| Cedrus libanoni | SCR | 0.6 ± 0.1 | 80 | 0 | 6 |
|  | ECB | no effect |  |  |  |
| Juniperus sabina | SCR | 0.9 ± 0.2 | 70 | 0 | 6 |
|  | ECB | 1.7 ± 0.3 | 75 | 0 | 6 |
| Picea abies | SCR | 0.9 ± 0.2 | 70 | 0 | 6 |
|  | ECB | 2.9 ± 0.7 | 60 | 0 | 6 |
| Picea banksiana | SCR | 0.9 ± 0.2 | 70 | 0 | 6 |
|  | ECB | 2.3 ± 0.6 | 70 | 0 | .6 |
| Picea jezoensis | SCR | 0.3 ± 0.1 | 90 | 0 | 6 |
|  | ECB | 3.5 ± 0.8 | 50 | 0 | 6 |
| Picea omorica | SCR | 0.5 ± 0.1 | 85 | 0 | 6 |
|  | ECB | no effect |  |  |  |
| Picea pungens | SCR | 0.7 ± 0.1 | 80 | 0 | 6 |
|  | ECB | no effect |  |  |  |
| Pinus ayacantha | SCR | 0.9 ± 0.2 | 70 | 0 | 6 |
|  | ECB | 3.4 ± 0.8 | 55 | 0 | 6 |
| Pinus nigra | SCR | 0.7 ± 0.3 | 80 | 0 | 6 |
|  | ECB | 2.4 ± 0.4 | 65 | 0 | 6 |
| Pinus rigida | SCR | 1.1 ± 0.4 | 65 | 0 | 6 |
|  | ECB | 3.3 ± 0.5 | 55 | 0 | 6 |
| Pinus sylvestris | SCR | 0.5 ± 0.2 | 85 | 0 | 6 |
|  | ECB | no effect |  |  |  |
| Thuya plicata | SCR | 0.8 ± 0.2 | 75 | 0 | 6 |
|  | ECB | 3.4 ± 0.8 | 55 | 0 | 6 |
| Lectins from the fruit body of the following fungus: |  | 0.7 ± 0.1 | 80 | 0 | 6 |
| Agaricus bisporus | ECB | no effect |  |  |  |
|  | SCR | 1.0 ± 0.4 | 60 | 0 | 6 |
| Lectin from the bark of: |  |  |  |  |  |
| Euonymus europaeus | ECB | 2.33.6 ± 1.0 | 50 | 0 | 6 |
|  | SCR | 0.7 ± 0.1 | 80 | 0 | 6 |

Not all lectins were screened at the same time or within the same groups. Comparisons between lectins is therefore inaccurate. Larval weights were analyzed based on control weights of each specific experiment, and not the combined control weight for all tests.
[1]Lectins were applied topically (2%) to Stoneville diet with larval weight and mortality recorded at seven days.
[2]ECB = European corn borer, SCR = Southern corn rootworm, and N.A = Not applicable.
[3]Weight is for surviving larvae (Mean ± SEM, n = surviving observations). The weight of ECB control larvae for all topical assays was 9.1 ± 1.8 mg (Mean ± SEM, n = 102) with 5% mortality. Control SCR larvae weight was 3.5 ± 0.4 mg (Mean ± SEM, n = 30) with 5% mortality.
[4]Percent weight loss is based on control weights of the day the compound was tested, not on the average of all control larvae for all test.
[5]Value has been adjusted for natural mortality and is based on number of insects, not observations.
[6]n = number of observations (usually 1 larvae observation −1).
*Value is significantly different from the control (on the days experiment took place) at the $p < 0.05$ level.

EXAMPLE 2

In another experiment, Stoneville media was prepared with only 90% of the original water. A 0.5% test composition was prepared using approximately 8.0 g of media and adding 45 mg of lectin in 1 mL PBS buffer. The media was then thoroughly mixed and poured into six cells. The addition of only 1 mL of buffer served as the control treatment. The cells were then infested and covered with mylar as described for the topical assays. Larval weights and mortalities were recorded at seven days and compared to the control treatment. If anti-insect activity was still observed at the 0.5% level, further tests were conducted at 0.3, 0.1, 0.05, and 0.01% levels of lectin incorporated in the dietary material. All percentages herein are by weight unless otherwise indicated.

Results

Results are shown in Table 3. Bioassays of WGA and BPA incorporated in larval dietary materials at 5 mg lectin per gram of diet showed 100% larval mortality. WGA produced 80% mortality at a level of 1 mg/g. BPA produced only 60% mortality at this level. The $LC_{50}$s were calculated to be 0.59 mg/g for WGA and 0.73 mg/g for BPA.

WGA also inhibited weight gain in surviving ECB larvae. Weight losses ranged form 90% near the $LC_{50}$ to 40% at the 0.1 mg/g level. BPA did not affect weight gain as dramatically as WGA. BPA inhibited growth by 50% at its $LC_{50}$.

Nine lectins of the 46 tested had toxic effects on SCR larvae. These were CFL, VVL, GSL, WGA, jacalin, MPL, EBL and PAL. BPA failed to produce any mortality when screened for seven days against SCR. However, WGA, CFL, jacalin, VVL, MPL, EBL and GSL inhibited growth of larval SCR by 40% or greater. All seven lectins showed inhibition of weight gain that was significant at the $p<0.05$ level. Larvae reared on diets containing CFL or MPL had the greatest reduction in growth of any treatment groups with an average weight of 0.2 mg. Larvae reared on diets containing jacalin, VVL, EBL and WGA had average weights of 0.4, 0.5, 0.6 and 0.6 mg, respectively. The control larvae had average weights of 1.4 mg ±0.1 mg.

TABLE 3

Effect of anti-insect lectins, incorporated into Stoneville diet, on growth and mortality of neonate European cornborer larvae[1].

| Lectin | Concentration[2] | % Mortality | % Weight Loss |
|---|---|---|---|
| BPA lectin | 0.5% | 90 | 99 |
|  | 0.1% | 25 | 65 |
|  | 0.05% | 13 | 35 |
|  | 0.01% | 0 | 10 |
| WGA | 0.5% | 100 | N.A. |
|  | 0.3% | 100 | N.A. |
|  | 0.1% | 80 | 99 |
|  | 0.05% | 50 | 90 |
|  | 0.03% | 7 | 90 |
|  | 0.01% | 0 | 45 |
| Bauhinia purpurea alba lectin | 0.5% | 90 | 99 |
|  | 0.1% | 25 | 65 |
|  | 0.05% | 13 | 35 |
|  | 0.01% | 0 | 10 |
| Triticum vulgare | 0.5% | 100 | N.A. |
|  | 0.3% | 100 | N.A. |
|  | 0.1% | 80 | 99 |
|  | 0.05% | 50 | 90 |
|  | 0.03% | 7 | 90 |
|  | 0.01% | 0 | 45 |
| Effect on Southern Corn Rootworm larvae: |  |  |  |
| Triticum vulgare lectin | 0.01% | 0 | 33 |
|  | 0.05 | 0 | 33 |
|  | 0.1 | 0 | 20 |
|  | 0.3 | 0 | 50 |
| Griffonia simplicifolia lectin II | 0.1 | 0 | 60 |
| Cicer arietinum lectin | 0.05 | 0 | 70 |
| Helix aspersa lectin | 0.1 | 0 | 70 |
| Jacalin | 0.1 | 0 | 75 |
| Helix Pomatia lectin | 0.1 | 0 | 75 |

[1]Weight and mortality were recorded at seven days.
[2]Concentration was percent of total weight of diet. Approximately 1.5 g of diet was used per observations.

Lectins from a variety of plant and animal sources as indicated below were screened for anti-insect activity against adult female potato leafhopper(*Empoasca fabae*).

TABLE 4

| Species | Common Name | M.W.(Kd) | Anti-Insect |
|---|---|---|---|
| WGA |  |  | Yes |
| Bauhinia purpurea |  |  | No |
| Artocarpus integrifolia |  |  | Yes |
| Pisum sativum |  |  | Yes |
| Lens culinaris |  |  | Yes |
| Phaseolus vulgaris (both E & L subunits) |  |  | Yes |
| E subunit only |  |  | Yes |
| L subunit only |  |  | No |
| Codium fragile |  |  | No |
| Glycine max |  |  | No |
| Bandeiraea simplicifolia II |  |  | No |
| Arachis hypogaea |  |  | No |

Industrial Applicability

I. Identification of the lectin gene and insertion into bacteria

In order to isolate the coding sequence for the lectin, it is necessary to have nucleotide sequence data which establishes an open reading frame (i.e., the correct triplet code for translation which should have only one "stop" signal at the very end of the gene.) It is also necessary to have an indication of where to look for the protease cleavage junction between the lectin and the replicase which precedes it in the sequence. This can be determined from the peptide sequence of the N-terminal portion of the lectin or by comparing the lectin sequence with that of other homologous lectins. This can generally be accomplished and the necessary information obtained without sequencing the entire gene. Once the sequence at both ends of the gene has been determined, the remainder of the gene can be cloned using restriction enzymes that flank the lectin coding region or, more preferably, by cloning the precise lectin coding region by oligonucleotide-directed amplification of DNA (polymerase chain reaction or PCR).

Once the gene has been isolated, it can be cloned into a bacterial expression vector with linkers added to create all three reading frames (using 8 mer, 10 mer, and 12 mers each of which contain an ATG translational start site). The resulting vectors, containing the fragments of interest, can be inserted into, for example, BRL's Maximum Efficiency DH5 F' IQ transformation competent *E. coli* cells. All three transformations, one for each linker, are then screened via minipreps for the presence and orientation of insert. Appropriate clones are then chosen to test for expression of the lectin gene.

Clones containing the properly oriented inserts are grown in culture medium conducive to the induction of the gene (LB medium with added IPTG). The cells are lysed and bacterial proteins are electrophoresed in SDS polyacrylamide gels and then transferred to nitrocellulose. The resulting protein blots are easily screened for presence of lectin using rabbit polyclonal and mouse monoclonal anti-lectin antibody.

Having determined the proper reading frame, it is then necessary to remove the gene from the bacterial expression vector. The linker at the start of the gene region supplies the necessary start codon.

II. Expression of the Lectin Gene in Plants

A plant expression cassette, employing the regulatory sequences developed by Beach, et al., and containing the lectin gene, is constructed. The restriction map of the preferred plasmid, designated pPHI414, is illustrated in FIG. 1. This plasmid contains an enhanced 35S promoter spanning nucleotides −421 to +2 of Cauliflower Mosaic Virus with the region from −421 to −90 duplicated in tandem, a 9 bp HindIII Sal1 fragment from pJII101 spanning the 5' leader sequence of Tobacco Mosaic Virus, a 579 bp fragment spanning the first intron from maize AdH1-S, and a 281 bp fragment spanning the polyadenylation site from the nopaline synthase gene in pTiT37.

Another construct which can be used as an expression cassette is the pPHI412 plasmid shown in FIG. 2. It differs from pPHI414 in that it lacks the AdH intron segment. However, like pPHI414, it is constructed to have numerous restriction sites between the O' segment and the NOS segment, which sites can be conveniently used for splicing any desired lectin structural gene into position.

The latter point is illustrated specifically by plasmid pPHI224, a 5.029 kb plasmid which is based on pPHI414 and contains the structural gene which codes substantially solely for wheat germ agglutinin.

This vector can be cotransformed with a similar plasmid containing a selectable marker for antibiotic resistance into Black Mexican Sweet corn protoplasts by electropotation. These protoplasts can then be induced to regenerate cell walls and develop into callus by conventional techniques. Likewise, this callus can then be subjected to antibiotic selection to select for transformed colonies, and these colonies can be tested for expression of lectin with antisera for the appropriate lectin using known methods. The efficiency of protection can be measured by infesting callus (or suspension cultures derived from callus) with the target insect and measuring survival percentages.

Results of this method are shown in Table 5

TABLE 5

The effect of Black Mexican Sweetcorn callus, transformed with a Wheat Germ Agglutinin gene[1]

| Callus line | WGA Ab | Wt.[2] | % loss[3] | % Mortality[4] |
|---|---|---|---|---|
| 2417 225 5-3 Control | Neg | 4.5 ± 1.4 | — | — |
| 2417 224 5-5 | Pos | 0.1 ± 0.05 | 95 | 50 |
| 2417 224 3-14 | Pos | 0.1 ± 0.05 | 95 | 10 |
| 2417 225 5-6 | Pos | 3.1 ± 2.0 | 30 | 50 |

[1]Each callus was infested with 3 larvae and weight and mortalities were taken at 7 days and compared with the control
[2]Weight is for surviving larvae (Mean ± SEM, n = surviving observations, max. n = 4).
[3]% loss is weight compared to that of control larve.
[4]Value has been adjusted for natural mortality and is based on number of insects, not observations.

6 other transformed lines that were positive for WGA had no effect on larval growth or mortality.

The lectin gene can be introduced into embryogenic maize callus by methods similar to those used for Black Mexican Sweet. Embryogenic callus can be regenerated to whole fertile plants. The insect resistance imparted by the endogenous production of the lectin is a simply inherited, dominant trait and can, if desired, be introduced into other plant varieties of the species by simple crossing or backcrossing.

III. Identification of the Receptor Protein in European Corn Borer

New fifth instar ECB larvae were infested on wheat germ diets containing 500 ppm of WGA, autoclaved WGA and *Bauhinea purpurea* lectin. Larvae were removed from 1 to 4 days later and dissected for removal of the midgut and peritrophic membrane. These organs were fixed in Karnovsky's solution, dehydrated in ethanol, critical point dried, and viewed using scanning electron microscopy.

Lectins that have been found to inhibit ECB growth were found to profoundly disrupt the peritrophic membrane. Autoclaved WGA had no effect on either growth or peritrophic membrane integrity. Other midgut cells showed no major abnormalities.

Separately, WGA, Bauhinea purpurea lectin, jacalin, and tomato lectin were biotinylated and used to probe a blot containing the proteins from the ECB whole midgut and midgut further dissected into portions representing the peritrophic membrane and the midgut minus the peritrophic membrane, separated on a Coomassie stained SDS-PVDF gel. (About 0.2 g of each frozen tissue was homogenized at 4 deg. C. in 0.5-1.0 mL PBS containing 5 mM CHAPS (3-cholamidopropyldimethylammonio-1-propanesulfonate) and protease inhibitors. The supernatant contained 1 μg/μL protein.)

Biotinylated WGA and Bauhinea lectin each intensely stained a band identifying a 22 Kd protein from the peritrophic membrane. This band was not stained differentially by biotinylated jacalin or tomato lectin. Although other bands were stained by all four materials, the band representing the 22 kd protein bound the larvicidal lectins differentially. Lectin binding to this protein appears to be responsible for disruption of the larval peritrophic membrane.

As used herein, the term "larvicidal amount" means an amount of the lectin sufficient to cause weight loss in 50% of treated larvae ($ED_{50}$) or mortality in 25% of treated larvae ($LD_{25}$)

What is claimed is:

1. A method for killing insect larvae which are susceptible to a lectin from

Artocarpus integrifolia (jacalin)
Bauhinia purpurea alba (camel's foot tree) (BPA)
Codium fragile (CFL)
Sambucus nigra (elderberry) bark (EBL)
Griffonia simplicifolia, lectin II (GSL)
Phytolacca americana (PAL)
Maclura pomifera (osage orange) (MPL)
Triticum vulgare (Wheat germ agglutinin, WGA)
Vicia villosa (VVL)
Cicer arietinum
Cystis scoparius
Helix aspersa
Helix pomatia
Mycoplasma gallisepticum
Phaseolus vulgaris E subunit
Urtica dioica
Tulip spp.
Eranthis hyemalis
Agropyrum repens leaf
Laburnum alpinum bark (GalNAc specific lectin)
Rhizoctonia solani
Listera ovata
Aegopodium podagraria
Amaranthus leucocarpus
Bryonia dioica
Limax flavus
Epipctis helleborine
Cymbidium hybrid
Psphopcarpus scandens (basic lectins 1 & 2)
Ceratobasidium cornigerum
Hordeum vulgate
Sedum spp.
Agave americana
Dieffenbachia spp.
Salix spp.
Crocus vernus
Populus canadiensis
Chamaecyparis lawsoniana
Platanus hybrid
Berberis spp.
Abies nobills
Abies pinsapo
Cedrus atlantica
Cedrus lebanoni
Juniperus sabina
Picea spp. needle
Pinus spp. needle
Sequoiadendron giganteum
Taxodium distichum
Thuya plicata
Agaricus bisporus fruit bodies
Acer pseudoplatanus bark
Epilobum angustifolium leaf
Euonymus europaeus bark
Pragmites australis leaf, or a combination of such lectins, comprising administering enterally to the larvae a larvicidal amount of the lectin or combination, wherein a composition comprising a larvicidal amount of said lectin or combination of lectins is applied to plants consumed by the larvae.

2. A method for killing insect larvae selected from European corn borer, corn rootworm and potato leafhopper, comprising administering enterally to the larvae a larvicidal amount of a lectin selected from jacalin, *Bauhinia purpurea alba* lectin, *Codium fragile* lectin, *Griffonia simplicifolia* II lectin, *Phytolacca americana* lectin, *Maclura pomifera* lectin, *Triticum vulgare* lectin (Wheat germ agglutinin), *Phaseolus vulgaris* lectin E subunit, *Crocus vernus* lectin, *Eranthis hyemalis* lectin, and *Vicia villosa* lectin and combinations thereof, wherein a composition comprising a larvicidal amount of said lectin or combination of lectins is applied to plants consumed by the larvae.

3. A method according to claim 2 wherein the lectin is administered enterally by incorporating the lectin or combination thereof in the diet of the larvae.

4. A method according to claim 3 wherein the diet of the larvae is the tissues of a living plant.

5. A method according claim 4 wherein the lectin or combination comprises a lectin which is not native to the plant.

* * * * *